United States Patent [19]

Nomura et al.

[11] 4,132,789

[45] Jan. 2, 1979

[54] 7-[2-(2-IMINO-4-THIAZOLIN-4-YL)-2-SULFOACETAMIDO]CEPHALOSPORINS AND ANTIBACTERIAL COMPOSITIONS CONTAINING THEM

[75] Inventors: Hiroaki Nomura, Osaka; Takenori Hitaka; Hiroshi Akimoto, both of Hyogo; Isao Minami, Osaka; Fumio Kiriki, Hyogo; Tatsuichi Matsuda, Osaka; Takeshi Fugono, Hyogo, all of Japan

[73] Assignee: Takeda Chemical Industries, Ltd., Japan

[21] Appl. No.: 715,495

[22] Filed: Aug. 18, 1976

[30] Foreign Application Priority Data

Aug. 25, 1975 [JP] Japan ................... 50-103327

[51] Int. Cl.² ................ A61K 31/545; C07D 501/46; C07D 501/34
[52] U.S. Cl. ............................. 424/246; 544/22; 544/25; 544/27; 544/28; 260/306.7 T
[58] Field of Search ............... 260/243 C; 424/246; 544/22, 25, 28

[56] References Cited

U.S. PATENT DOCUMENTS

| 3,988,327 | 10/1976 | Ishiguro et al. | 260/243 C |
| 4,008,246 | 2/1977 | Ochiai et al. | 260/243 C X |
| 4,065,619 | 12/1977 | Morimoto et al. | 544/25 |

*Primary Examiner*—Jose Tovar
*Assistant Examiner*—Diana G. Rivers
*Attorney, Agent, or Firm*—Craig & Antonelli

[57] ABSTRACT

Novel cephalosporins shown by the general formula:

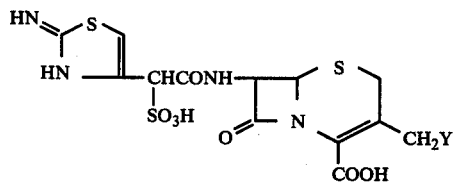

wherein Y is an acyloxy group, a quaternary ammonium group or a group of the formula: —S—R in which R is a nitrogen-containing heterocyclic group, and pharmaceutically acceptable salts thereof have high antibacterial properties against Gram-positive and Gram-negative bacteria including *Pseudomonas aeruginosa* and *Serratia marcescens*.

7 Claims, No Drawings

7-[2-(2-IMINO-4-THIAZOLIN-4-YL)-2-SULFOACETAMIDO]CEPHALOSPORINS AND ANTIBACTERIAL COMPOSITIONS CONTAINING THEM

The present invention relates to novel antibiotics. More particularly, the present invention relates to cephalosporins represented by the general formula [I]:

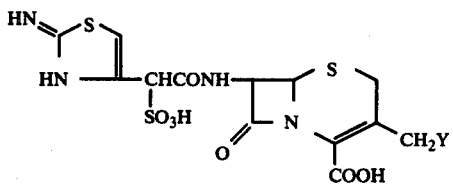

wherein Y is an acyloxy group, a quaternary ammonium group or a group of the formula: — S — R in which R is a nitrogen-containing heterocyclic group, and pharmaceutically acceptable salts thereof. The present invention also relates to method for the production of said cephalosporins and pharmaceutically acceptable salts thereof.

Since the discovery of cephalosporin C, cephalosporin antibiotic compounds have been the subjects of intensive studies, the studies being centered around the chemical modification of the 7- and 3-positions of the cephem ring. Despite the fact that the number of known semi-synthetic cephalosporins thus obtained is literally vast, there is only a limited number of compounds that have anti-Serratia or anti-Pseudomonas activity.

We discovered that the novel cephalosporins of the general formula [I] given hereinbefore are not only effective in the treatment of infectious diseases caused by a broad spectrum of gram-positive and gram-negative bacteria but also display high activity against microorganisms of the genus Serratia and Pseudomonas. This invention has been made on the basis of the above finding.

Thus, the first object of the present invention is to provide novel cephalosporin compounds which are highly antibacterial.

The second object of the present invention is to provide an industrially feasible method for the production of the cephalosporin compounds.

The third object of the present invention is to provide a medicinal composition for the therapy of diseases caused by the infectious bacteria containing as an active ingredient the cephalosporin compound.

As to the substituent represented by Y in the general formula [I], the acyloxy group is exemplified by acetyloxy, propionyloxy, 3-oxobutyryloxy, 3-carboxypropionyloxy, 2-carboxybenzoyloxy, 4-carboxybutyryloxy, mandelyloxy, 2-(carbethoxycarbamoyl)-benzoyloxy, 2-(carbethoxysulfamoyl)benzoyloxy, 3-ethoxycarbamoylpropionyloxy and so forth. The acyloxy group represented by Y is preferably an acyl group of 2 to 20 carbon atoms.

The quaternary ammonium group is exemplified by a substituted or unsubstituted pyridinium, picolinium, quinolinium or lutidinium, the substituent being alkyl, halogen, carbamoyl, N-hydroxyalkylcarbamoyl, N-carboalkoxycarbamoyl, N-cyanocarbamoyl, carboxyalkyl, halogenated alkyl or hydroxyalkyl. In the above, said alkyl includes an alkyl of 1 to 4 carbon atoms such as methyl, ethyl, n-propyl, isopropyl, etc.; said alkoxy includes an alkoxy of 1 to 4 carbon atoms such as methoxy, ethoxy, n-propoxy, isopropoxy, etc.; and said halogen includes chlorine, bromine, etc. As the preferred quaternary ammonium group may be mentioned pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-(N-carbomethoxycarbamoyl)pyridinium, 4-(N-cyanocarbamoyl)pyridinium, 4-(carboxymethyl)pyridinium, 4-(hydroxymethyl)pyridinium, 4-(trifluoromethyl)pyridinium, quinolinium, picolinium and lutidinium.

The nitrogen-containing heterocyclic group represented by R in the substituent -S-R is preferably a five- or six-membered heterocyclic ring containing 1 to 4 hetero-atoms selected from the group consisting of oxygen, sulfur and nitrogen, which is commonly exemplified by pyridyl, N-oxidepyridyl, pyrimidyl, pyridazinyl, N-oxide-pyridazinyl, pyrazolyl, diazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl and so forth.

These heterocyclic ring may carry one or more substituents such as alkyl groups, e.g. methyl, ethyl, propyl, etc.; alkoxy groups, e.g. methoxy, ethoxy, etc.; halogens, e.g. chlorine, bromine, etc.; halogen-substituted alkyl groups, e.g. trifluoromethyl, trichloroethyl, etc.; hydroxyl; mercapto; amino; carboxyl; carbamoyl; morpholino; sulfo; alkoxycarbonyl; mono-, di- and trialkylaminoalkyl groups, e.g. dimethylaminoethyl, etc.; mono- and dialkylcarbonylalkyl groups; alkylthioalkyl groups, e.g. methylthiomethyl, etc.; mercapto or amino groups substituted by such substituted alkyl groups as mentioned above; and so forth. In the above, said alkyl is preferably an alkyl of 1 to 3 carbon atoms and said alkoxy is preferably an alkoxy of 1 to 3 carbon atoms.

The most preferred nitrogen-containing heterocyclic groups are

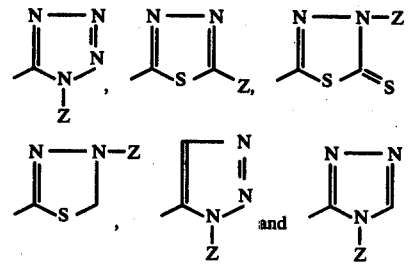

wherein Z is a member selected from the group consisting of hydrogen, alkyl, mercapto, dialkylaminoalkyl, dialkylaminoalkylthio and amino, said alkyl being preferably an alkyl of 1 to 3 carbon atoms such as methyl, ethyl, n-propyl, isopropyl, etc.

The cephalosporins of the general formula [I] have the acid groups, e.g. 4-carboxyl group and sulfo group in the acyl group of 7 position. They may be free or in the form of pharmaceutically acceptable salts with nontoxic bases. The nontoxic bases for pharmaceutically acceptable salts are well known in the field of cephalosporins, and are exemplified by alkali metal or alkaline earth metal hydroxide, carbonate or bicarbonate; the alkali or alkaline earth metal including sodium, potassium, calcium, magnesium, etc.; basic amino acid, e.g.

arginine, ornithinine, lysine, histidine, etc.; and polyhydroxyalkylamine, e.g. N-methylglucamine, diethanolamine, triethanolamine, tris-hydroxymethylaminomethane; etc.

When the substituent group Y includes a quaternary ammonium group, the acid groups may form a betaine linkage with the quaternary ammonium group. In case when the cephalosporin [I] is in the free form, the sulfo group preferentially forms the betaine linkage with the quaternary ammonium group, but in case when the sulfo group forms a salt with a base (e.g. alkali metal hydroxide such as sodium hydroxide, potassium hydroxide; etc.), the remaining free carboxyl group forms the betaine linkage with the quaternary ammonium group.

The imino groups in the thiazolidine ring of the cephalosporins [I] may be also free or in the form of pharmaceutically acceptable salts with acids, which are exemplified by mineral acids e.g. hydrochloric acid, sulfuric acid, nitric acid, etc. and organic acid e.g. oxalic acid, acetic acid, etc.

The cephalosporin [I] and pharmaceutically acceptable salt thereof may be produced by a method which is known per se.

Thus, the processes for the production of cephalosporin compounds [I] and their pharmaceutically acceptable salts are exemplified by:

(1) A process for producing a cephalosporin of the above formula [I] or pharmaceutically acceptable salt thereof, characterized in that said process comprises reacting a compound of the formula [II]:

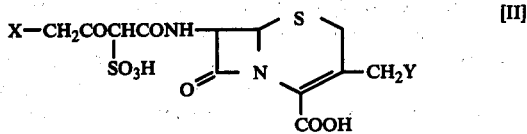

[wherein X is halogen; Y has the same meaning as defined above] or a salt thereof with thiourea or a salt thereof;

(2) A process for producing a compound of the formula [I']:

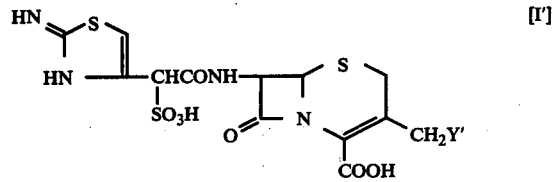

[wherein Y' is a quaternary ammonium group or a group of the formula: —S—R in which R is a nitrogen-containing heterocyclic group] or a pharmaceutically acceptable salt thereof, characterized in that said process comprises reacting a compound of general formula [III]:

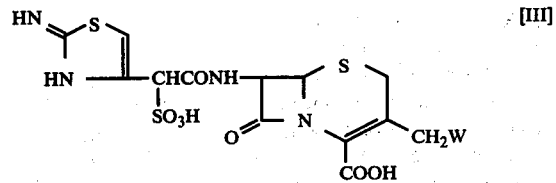

[wherein W is an acyloxy group] or a salt thereof with a tertiary amine, a mercapto compound of the formula: HS-R [wherein R is a nitrogen-containing heterocyclic group] or any of respective salts; and (3) A process for producing a compound of the general formula [I] or pharmaceutically acceptable salt thereof, characterized in that said process comprises reacting a compound of the general formula [IV]:

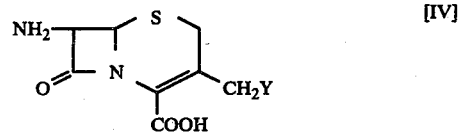

[wherein Y has the same meaning as defined above] or a salt thereof with 2-sulfo-2-(2-imino-4-thiazolin-4-yl)acetic acid, a salt thereof or a reactive derivative thereof.

The starting material compound [II] employed in the first process according to this invention may for example be produced by reacting a γ-halogenoacetyl halide with a compound of formula [IV] in a manner conventional per se and subjecting the resultant compound of the general formula [V]:

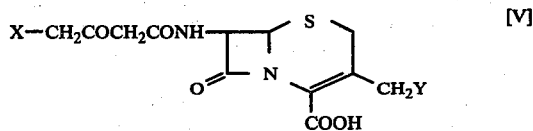

[wherein symbols X and Y have the same meanings as defined hereinbefore] to a reaction by which a sulfo group is introduced, or alternatively by subjecting γ-halogenoacetyl halide to a reaction by which a sulfo group is introduced and then reacting the resulting compound with a compound of formula [IV]. Said reaction by which a sulfo group is introduced may be easily accomplished by permitting sulfuric anhydride to act on the substrate compound in an inert solvent. Said sulfuric anhydride may be used in such forms as, for example, $SO_3$, $SO_3$-dioxane, $SO_3$-ether, $SO_3$-triethylamine, $SO_3$-pyridine complex and so forth, it being normally preferable to employ one mole equivalent or a slight excess of sulfuric anhydride based on the substrate compound. The inert solvent is exemplified by methylene chloride, dimethylsulfoxide, tetrahydrofuran, dioxane and pyridine. The reaction proceeds smoothly at and below room temperature, although it may be conducted under heating or cooling if desired. The reaction normally goes to completion in 10 minutes to 24 hours.

The resultant compound [II] is reacted with thiourea to obtain the compound [I]. The compound [II] need not always be isolated but the reaction mixture containing the same may be subjected to the reaction either directly or after some previous purification process. Said thiourea is subjected to the reaction normally as the free compound or in the form of a salt at its thiol function, with an alkali metal, e.g. lithium, sodium or potassium, or as an ammonium salt. The compound [II] may be used in the free form or in the form of a salt with the alkali metal hydroxides, e.g. sodium hydroxide, potassium hydroxide, etc. or an organic amine, e.g. trimethylamine, triethylamine, etc.

The reaction is normally effected by incorporating 1 to 6 molecular equivalents of thiourea with one molar equivalent of the compound [II] in the presence of a solvent. Among the solvents suitable for this purpose are water and the common organic solvents which do not interfere with the reaction such as methanol, ethanol, acetone, dioxane, acetonitrile, chloroform, ethylene chloride, tetrahydrofuran, ethyl acetate, dimethylformamide, dimethylacetamide and so forth. Of these solvents, hydrophilic solvents may be employed in admixture with water. The reaction may also be carried out in the presence of a base which is exemplified by alkali metal hydroxides, e.g. sodium hydroxide, potassium hydroxide, etc.; alkali metal carbonates, e.g. sodium carbonate, potassium carbonate, etc.; organic tertiary amines, e.g. trimethylamine, triethylamine, pyridine and so forth. While the reaction temperature is largely optional, the reaction is preferably carried out normally within the range of 100 to $-10°$ C. and, for still better results, within the range of 40 to $0°$ C. The reaction normally proceeds fast and goes to completion within a few hours.

The second process comprises reacting a compound of formula [III] with a tertiary amine or a mercapto compound of the formula: HS—R in which R has the same meaning as defined above. The compound [III] may be employed in its free form or as a salt with a base such as a salt of an alkali metal, e.g. sodium, potassium or the like or of an organic amine, e.g. trimethylamine, triethylamine or the like. Where the mercapto compound is employed, it is subjected to the reaction as the free mercapto compound or as a salt at its —SH function, e.g. the salt of an alkali metal such as lithium, sodium or potassium. This reaction is effected in the neighborhood of neutral pH and at a temperature ranging from room temperature to an elevated temperature in the range of about 40 to $80°$ C. The reaction is conducted in a solvent. The solvent is preferably an aqueous solvent such as water or a mixture of water and a highly polar solvent which does not interfere with the reaction such as acetone, tetrahydrofuran, dimethylformamide, methanol, ethanol, dimethylsulfoxide and so forth. Where [III] is employed in the free form, it is sometimes desirable to adjust the reaction system to neutral pH by adding a base to the system, said base being exemplified by sodium hydrogen carbonate, potassium hydrogen carbonate, sodium carbonate, potassium carbonate and so forth. If desired, a buffer solution may also be employed. The reaction time and other conditions are determined by reference to the starting materials, solvent, temperature and other factors. By way of illustration, the reaction may be carried out by reacting the compound [III] with 1 to several molecular equivalents of the tertiary amine or the mercapto compound in the presence of a polar solvent (water or an aqueous organic solvent) either at room temperature or at an elevated temperature up to $80°$ C. for a time ranging from a few hours to a few days. This reaction may be carried out in the presence of scores of molecular equivalents of KSCN or an inorganic salt such as KI. The tertiary amine reacts with acyloxy group of the compound [III] to form the quaternary ammonium group mentioned above, and the kind of the tertiary amine is determined in accordance with the kind of the contemplated quaternary ammonium group. As examples of the tertiary amine and the mercapto compound, there may be mentioned pyridine, nicotinamide, isonicotinamide, 5-mercaptotetrazole, 5-mercapto-1-methyltetrazole, 5-mercapto-2-methyltetrazole, 5-methyl-2-mercapto-1,3,4-thiadiazole, 2,5-dimercapto-1,3,4-thiadiazole and so forth.

The third process comprises acylating a compound of formula [IV] with 2-sulfo-2-(2-imino-4-thiazolin-4-yl)acetic acid, its salt or its reactive derivative. The starting material 2-sulfo-2-(2-imino-4-thiazolin-4-yl)acetic acid may be produced, for example, by reacting a γ-halogenoacetoacetate (X—CH$_2$COCH$_2$COOR', where R' is alkyl, e.g. methyl, ethyl or the like, benzyl, phenyl or the like, and X is halogen) with sulfuric anhydride in the same manner as hereinbefore described, reacting the resultant γ-halogeno-α-sulfoacetoacetate with thiourea and hydrolyzing the reaction product with alkali or acid. The said starting compound may also be produced by sulfonating the γ-halogenoacetoacetic acid directly and, then, causing the sulfonated product to undergo cyclization with thiourea. Another process comprises introducing a sulfo group to a γ-halogenoacetoacetonitrile or γ-halogenoacetoacetamide, causing the sulfonate product further to undergo cyclization with thiourea and hydrolyzing the cyclization product with acid or alkali. The 2-sulfo-2-(2-iminothiazolin-4-yl)acetic acid is employed as the free acid or as a reactive derivative thereof. Thus, the compound may be subjected to the acylation reaction as the free acid or as a salt, with sodium, potassium, calcium, trimethylamine, pyridine or the like or as a reactive derivative such as an acid halide, acid anhydride, mixed acid anhydride, active amide or ester thereof. The activated ester just mentioned may for example be p-nitrophenyl ester, 2,4-dinitrophenyl ester, pentachlorophenyl ester, N-hydroxysuccinimide ester or N-hydroxyphthalimide ester. As examples of said mixed acid anhydride, there may be mentioned mixed acid anhydrides with carbonic acid monoesters, e.g. monomethyl carbonate or monoisobutyl carbonate and mixed acid anhydrides with lower alkanoic acids which may optionally be halogenated, e.g. pivalic acid or trichloroacetic acid. When the free acid or salt is employed, use is made of a suitable condensing agent such as N,N'-di-substituted carbodiimides, e.g. N,N'-dicyclohexylcarbodiimide, azolide compounds, e.g. N,N'-carbonylimidazole, N,N'-thionyldiimidazole, etc.; dehydrating agents, e.g. N-ethoxycarbonyl-2-ethoxy-1,2-dihydroquinoline, phosphorus oxychloride, alkoxyacetylene and so forth. Where such a condensing agent is employed, the reaction seems to proceed through the formation of a reactive derivative of the carboxylic acid. In conducting the reaction, it is preferable to protect the imino groups of the compound [IV] beforehand. Commonly employed are the imino groups substituted by acyl groups that can be easily removed under mild conditions (e.g. under mild acid or alkaline conditions, catalytic or other reductive conditions, etc.), such as formyl, amyloxycarbonyl, t-butoxycarbonyl, 2,2,2-trichloroethoxycarbonyl, benzyloxycarbonyl, p-nitrobenzyloxycarbonyl, 2-methylsulfonylethoxycarbonyl and so forth, or the imino groups protonated by salt formation with acid such as hydrochloric acid, sulfuric acid, formic acid or acetic acid.

The compound [IV] may be such that its 4-carboxyl group has been made into a salt such as the salt of an alkali metal, alkaline earth metal or organic amine, e.g. sodium, potassium, magnesium, calcium, aluminum, triethylamine or the like; an ester which can be easily converted to a carboxyl group by treatment with alkali or acid, enzymatic treatment, reduction or other procedure, or which as such display activity in vivo as the ester of the end product [I]. The ester includes 2-methylsulfonylethyl ester, trimethylsilyl ester, dimethylsilenyl ester, benzhydryl ester, 2,2,2-trichloroethyl ester, phenacyl ester, p-methoxybenzyl ester, p-nitrobenzyl ester, methoxymethyl ester or the like.

This reaction may commonly be conducted with advantage and smoothly in a solvent. As the solvent, there may be mentioned any of the common solvents and mixtures of such solvents which do not interfere with the reaction of the invention, such as water, acetone, diisobutyl ketone, tetrahydrofuran, ethyl acetate, dioxane, acetonitrile, chloroform, dichloromethane, dichloroethylene, pyridine, dimethylaniline, dimethylformamide, dimethylacetamide, dimethylsulfoxide and so forth. While the reaction temperature is not very critical, the reaction is commonly carried out under cooling or at room temperature. Where the reaction is carried out under the elimination of an acid, it may be conducted in the presence of a base. As the common examples of such base, there may be mentioned aliphatic, aromatic and heterocyclic nitrogen-containing bases, alkali metal carbonates and alkali metal hydrogen carbonates, such as triethylamine, N,N-dimethylaniline, N-ethylmorpholine, pyridine, collidine, 2,6-lutidine, sodium carbonate, potassium carbonate, sodium hydrogen carbonate, potassium hydrogen carbonate and so forth. The reaction may be carried out in an inert gaseous atmosphere, e.g. nitrogen gas.

The resultant cephalosporin derivative [I] is subjected, if desired, to a procedure for removal of the protective group which is known per se before it is isolated and purified by a conventional procedure such as solvent extraction, pH adjustment, phasic transfer, distillation, crystallization, recrystallization or/and chromatography (on polystyrene, sulfonated polystyrene or other resin). Where the imino group of starting compound has been protected in acid-protonated form, the free imino compound [I] may be easily obtained in the course of purification or by the pH adjustment. Where the imino group has been protected by an acyl group, the free imino compound [I] may be obtained by a conventional deacylation procedure appropriate to the particular acyl group, e.g. acid treatment in the case of formyl, amyloxycarbonyl or t-butoxycarbonyl; reduction for 2,2,2-trichloroethoxycarbonyl, benzyloxycarbonyl and p-nitrobenzyloxycarbonyl; or alkali treatment where the acyl group is 2-methylsulfonylethoxycarbonyl.

The novel cephalosporins [I] thus obtained are antibiotic agents having a broad spectrum of activity against gram-positive and gram-negative bacteria of the genus Pseudomonas (e.g. *Pseudomonas aeruginosa*) and the genus Serratia (e.g. *Serratia marcescens*). Thus, the spectrum of these new antibiotics includes antibacterial properties against *Escherichia coli*, *Klebsiera pneumoniae* and organisms of the genus Proteus. These agents display increased activity against those infectious bacteria. The cephalosporins of the present invention are low toxic and can be well tolerated. The cephalosporins of the present invention may be processed into solutions or suspensions for use as injections, or further in admixture with a conventional basis, used as medications for external application. More particularly, cephalosporins of the present invention, for example 7-[2-(2-imino-4-thiazolin-4-yl)-2-sulfoacetamido]-3-(4-carbamoyl-pyridinium)methyl-3-cephem-4-carboxylic acid betaine are used through injection against Pseudomonas infections at a dose level of 10 to 200 mg/kg daily, preferably in the range of 20 to 70 mg/kg daily per adult human; or against Escherichia infections at a dose level of 5 to 100 mg/kg daily, preferably in the range of 5 to 50 mg/kg daily per adult human, in 3 to 5 divided doses a day. Against infections with other gram-negative or gram-positive bacteria, these antibiotics may be used substantially in the same manner as the known cephalosporins such as "Cephalotin".

EXAMPLE 1

Process for production of sodium 7-[2-(2-imino-4-thiazolin-4-yl)-2-sulfoacetamido[-3-acetoxymethyl-3-cephem-4-carboxylate 12 ml of methylene chloride containing 1.31 g of sulfuric anhydride-dioxane complex is cooled to 0° C. and, under stirring 2.34 g of 7-(γ-chloroacetoacetamido)-3-acetoxymethyl-3-cephem-4-carboxylic acid is added in small installments over a period of about 10 minutes. The reaction mixture is allowed to return to room temperature and left standing for 1 hour. Then, after cooling to −10° C., 30 ml of ethanol, 547 mg of thiourea and 1.13 g of anhydrous sodium acetate are added. The mixture is allowed to return to room temperature again and left standing overnight. The solvent is distilled off under reduced pressure and the residue is diluted with 50 ml of water and adjusted to pH 7.0 with 1N-NaOH. The solution is chromatographed on a column of polystyrene resin (Amberlite XAD-II), elution being carried out with water. The fractions rich in the contemplated compound are pooled and lyophilized. By the above procedure is obtained the captioned compound.

IR($cm^{-1}$, KBr): 1762, 1665, 1610, 1580, 1230, 1043
NMR(in $D_2O$, δ): 2.17(s,3H), 3.60(m,2H), 4.85(d-q,2H), 5.10(s,1H), 5.18(d,1H), 5.76(d,1H), 7.00(s,1H)

EXAMPLE 2

Synthesis of sodium 7-[2-(2-imino-4-thiazolin-4-yl)-2-sulfoacetamido]-3-cephem-3-(1-methyltetrazol-5-yl)thiomethyl-4-carboxylate 6.68 g of $SO_3$-$CH_2Cl_2$ solution (8.32 g $SO_3$/62 g $CH_2Cl_2$) is cooled to 0° C. and a solution of 1.01 g of dried dioxane in 5 ml of $CH_2Cl_2$ is added. Under cooling with ice and stirring, 2.02 g of 7-(γ-chloroacetamido)-3-chephem-3-(1-methyltetrazol-5-yl)thiomethyl-4-carboxylic acid is added in small installments over a period of about 10 minutes. The mixture is stirred at room temperature for 1 hour. The reaction mixture is cooled to −20 to −10° C. with ethanol-dry ice and immediately after addition of 25 ml of cold ethanol, 0.41 g of thiourea and 1.84 g of anhydrous sodium acetate are added. The mixture is allowed to return to room temperature, stirred and allowed to stand overnight.

The solvent is then distilled off and the dry residue is diluted with 75 ml of cold water and adjusted to pH 6.7 with 1N-NaOH. The insolubles are filtered off and the filtrate is lyophilized. The resultant powder is dissolved in a small amount of water and chromatographed on 900 ml of a column of polystyrene resin (Amberlite XAD-II). Elution is carried out with water and the fractions rich in the contemplated compound are pooled and lyophilized. By the above procedure is obtained sodium 7-[2-(2-imino-4-thiazolin-4-yl)-2-sulfoacetamido]-3-cephem-3-(1-methyltetrazol-5-yl)thiomethyl-4-carboxylate.

IR(cm$^{-1}$, KBr): 3400, 1755, 1660, 1600, 1520, 1220, 1045 NMR(in D$_2$O, δ): 3.60(q,2H), 4.04(s,3H), 3.97(q,2H) 5.07(s,1H), 5.10(d,1H), 5.07(d,1H), 6.90(s,1H)

EXAMPLE 3

Process for production of 2-sulfo-2-(2-imino-4-thiazolin-4-yl)acetic acid.

10 ml of methylene chloride containing 2.52 g of sulfuric anhydride-dioxane complex is cooled to 0° C. and, under stirring, 1.65 g of ethyl γ-chloroacetoacetate is added. The reaction mixture is allowed to return to room temperature, stirred for 1 hour and cooled to −10° C. Following the addition of 25 ml of ethanol and 1.14 g of thiourea, the mixture is allowed to return to room temperature again and is stirred continuously for 2 days. The reaction mixture is cooled on an ice-bath and the resultant white crystals are collected by filtration, rinsed with small amounts of ethanol and, then, of ether and finally dried. By the above procedure is obtained ethyl (2-imino-4-thiazolin-4-yl)-2-sulfoacetate. IR(cm$^{-1}$, KBr): 1743, 1654, 1608, 1590, 1208, 1193, 1053 NMR(DMSO-d$_6$, δ): 1.19(t,3H), 4.10(q,2H), 4.86(s,1H), 6.86(s,1H)

Under cooling with ice and stirring, 798 mg of the above ethyl (2-imino-4-thiazolin-4-yl)-2-sulfoacetate is added to 6.6 ml of 1N-sodium hydroxide and the mixture is allowed to stand for 15 minutes. Then, under cooling with ice and stirring, the mixture is neutralized with 7.0 ml of 1N hydrochloric acid, whereupon white precipitate is obtained. The precipitate is recovered by filtration, rinsed with ethanol and ether and dried. By this procedure is obtained 620 mg of 2-sulfo-2-(2-imino-4-thiazolin-4-yl)acetic acid. IR(cm$^{-1}$, KBr): 1732, 1628, 1603, 1576, 1230, 1190, 1050 NMR(NaHCO$_3$ in D$_2$O, δ): 4.93(s,1H), 6.90(s,1H)

EXAMPLE 4

Process for production of 7-[2-(2-imino-4-thiazolin-4-yl)-2-sulfoacetamido]-3-(4-carbamoylpyridinium)methyl-3-cephem-4-carboxylic acid betaine In 1.0 ml of water is dissolved 371 mg of 7-amino-3-(4-carbamoylpyridinium)methyl-3-cephem-4-carboxylic acid betaine hydrochloride together with 84 mg of sodium hydrogen carbonate, followed by addition of 40 ml of dimethylformamide. Under cooling with ice and stirring, 238 mg of 2-sulfo-2-(2-imino-4-thiazolin-4-yl)acetic acid and 206 mg of dicyclohexylcarbodiimide are added. The reaction mixture is allowed to return to room temperature and, then, stirred continuously for 4 hours. The mixture is diluted with 25 ml of water and adjusted to substantial neutrality with about 84 mg of sodium hydrogen carbonate. The white precipitate is filtered off and the filtrate is lyophilized. The procedure provided a pale yellowish powder. This product is chromatographed on a column of polystyrene resin (Amberlite XAD-II), elution being carried out with water. The fractions rich in the contemplated product are pooled and lyophilized. By the above procedure is obtained the captioned compound.

IR(cm$^{-1}$, KBr): 1760, 1675, 1615, 1510, 1210, 1045 NMR(in D$_2$O, δ): 3.42(q,2H), 5.06(s,1H), 5.20(d,1H), 5.50(q,2H), 5.76(d,1H), 6.89(s,1H), 8.37(d,2H), 9.15(d,2H)

EXAMPLE 5

Process for production of sodium 7-[2-(2-imino-4-thiazolin-4-yl)-2-sulfoacetamido]-3-(2-methyl-1,3,4-thiadiazol-4-yl)-thiomethyl-3-cephem-4-carboxylate In 2.0 ml of water is dissolved 536 mg of sodium 7-[2-(2-imino-4-thiazolin-4-yl)-2-sulfoacetamido]-3-acetoxymethyl-3-cephem-4-carboxylate together with 120 mg of 2-methyl-5-mercapto-1,3,4-thiadiazole and 101 mg of sodium hydrogen carbonate. The mixture is heated at 60° C. for 3 hours. After the reaction, it is chromatographed on a column of polystyrene resin (Amberlite XAD-II) elution being carried out with water. The fractions rich in the contemplated product are pooled and lyophilized. By the above procedure is obtained the captioned compound as white or pale yellowish powder.

IR(cm$^{-1}$, KBr): 1760, 1665, 1605, 1220, 1040 NMR(in D$_2$O, δ): 2.70(s,3H), 3.40(q,2H), 4.05(q,2H), 5.08(s,1H), 5.10(d,1H), 5.75(d,1H), 6.85(s,1H)

EXAMPLE 6

By a procedure similar to that described in Example 2, 4 or 5, the 3-substituted cephalosporanic acid derivatives listed below in Table 1 are synthesized.

Table 1

[Structure: HN=C(NH)-S-C(=CH-CONH-)-CH(SO$_3$Na)-CONH- attached to cephem nucleus with -CH$_2$X at 3-position and COOY at 4-position]

(where X includes a quaternary ammonium group, Y = − ; otherwise, Y = Na)

| X | NMR (60Mc, D$_2$O, δ value) |
|---|---|
| [thiadiazole]-SH | 3.40(d-q,2H), 4.05(q,2H), 5.02(d,1H), 5.69(d,1H), 5.00(s,1H), 6.80(s,1H) |
| [thiadiazole]-SCH$_2$CH$_2$N(CH$_3$)$_2$ | 2.74(s,6H), 3.44(b-m,6H), 6.34(q,2H), 5.00(d,1H), 5.56(d,1H), 5.00(s,1H), 6.85(s,1H) |
| [thiadiazole]-NH$_2$ | 3.45(q,2H), 4.04(q,2H), 5.05(d,1H), 5.67(d,1H), 5.02(s,1H), 6.85(s,1H) |
| [thiadiazole N-CH$_3$, =S] | 3.36(q,2H), 4.14(q,2H), 5.00(d,1H), 5.76(d,1H), 3.70(s,3H), 5.01(s,1H), 6.90(s,1H) |
| [thiadiazole with CH$_2$CH$_2$N(CH$_3$)$_2$] | 2.79(s,6H), 3.55(q,2H), 3.58(b-t,2H), 4.25(q,2H), 4.75(b-t,2H), 5.09(d,1H), 5.65(d,1H), 5.10(s,1H), 6.90(s,1H) |
| [thiadiazole-NH$_2$, =S] | 3.48(q,2H), 4.15(q,2H), 5.08(d,1H), 5.71(d,1H), 5.05(s,1H), 6.85(s,1H) |
| [imidazole type, NH] | 3.40(q,2H), 4.05(q,2H), 3.10(d,1H), 5.75(d,1H), 5.08(s,1H), 6.90(s,1H), 8.02(s,1H) |

Table 1-continued

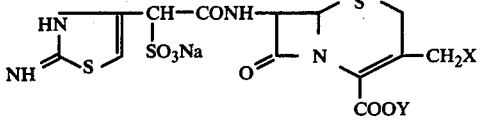

(where X includes a quaternary ammonium group, Y = -;
otherwise, Y = Na)

| X | NMR (60Mc, D$_2$O, δ value) |
|---|---|
| 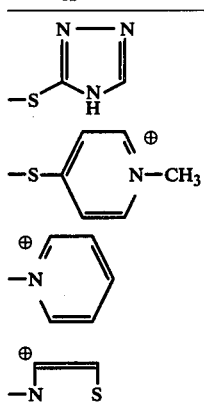 | 3.38(q,2H), 4.10(q,2H), 5.09(d,1H), 5.72(d,1H), 5.06(s,1H), 6.87(s,1H), 8.36(s,1H) |
| -S-⟨pyridinium⟩N—CH$_3$ | 3.39(q,2H), 4.16(q,2H), 5.04(d,1H), 5.66(d,1H), 4.15(s,3H), 5.06(s,1H), 6.90(s,1H), 7.72-8.32(m,4H) |
| -N⟨pyridinium⟩ | 3.46(q,2H), 5.10(d,1H), 5.71(d,1H), 5.43(b-q,2H), 5.08(s,1H), 6.90(s,1H), 8.00-9.00(m,5H) |
| -N⟨thiazolium⟩S | 3.45(q,2H), 5.10(d,1H), 5.73(d,1H), 5.30(b-q,2H), 5.05(s,1H), 6.85(s,1H), 8.17(b-d,1H), 8.36(b-d,1H), 10.00(b-s,1H) |

We claim:

1. A cephalosporin represented by the formula:

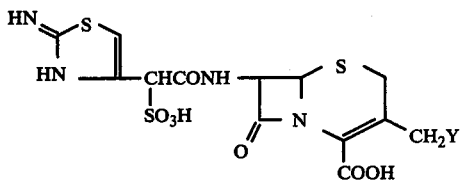

wherein Y is an acetoxy group, or a substituted or unsubstituted pyridinium, picolinium, quinolinium or lutidinium, the substituent being alkyl, halogen, carbamoyl, N-hydroxyalkyl, N-carboalkoxycarbamoyl, N-cyanocarbamoyl, carboxyalkyl, halogenated alkyl or hydroxyalkyl, the alkyl or alkoxy group in the substituent having from 1 to 4 carbon atoms, or a pharmaceutically acceptable salt thereof.

2. A cephalosporin as claimed in claim 1, wherein the acyloxy group is acetoxy.

3. A cephalosporin as claimed in claim 1, wherein Y is pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-(N-carbomethoxycarbamoyl)pyridinium, 4-(N-cyanocarbamoyl)-pyridinium, 4-(carboxymethyl) pyridinium, 4-(hydroxymethyl)-pyridinium, 4-(trifluoromethyl)pyridinium, quinolinium, picolinium or lutidinium.

4. A cephalosporin as claimed in claim 1, wherein Y is 4-carbamoylpyridinium.

5. A cephalosporin as claimed in claim 1, wherein Y is pyridinium-1-.

6. A cephalosporin represented by the formula:

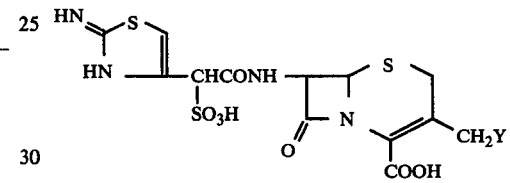

wherein Y is thiazolium-3-, or a pharmaceutically acceptable salt thereof.

7. A medicinal composition for the therapy of diseases caused by bacteria which contains as an active ingredient an effective amount of the cephalosporin or pharmaceutically acceptable salt thereof claimed in claim 1.

* * * * *